US008435942B2

(12) United States Patent
Perricone et al.

(10) Patent No.: US 8,435,942 B2
(45) Date of Patent: May 7, 2013

(54) METHODS FOR FORMULATING STABILIZED INSULIN COMPOSITIONS

(75) Inventors: Nicholas V. Perricone, Meriden, CT (US); Chim Potini, Bloomington, IL (US)

(73) Assignee: Transdermal Biotechnology, Inc., Meriden, CT (US)

(*) Notice: Subject to any disclaimer, the term of this patent is extended or adjusted under 35 U.S.C. 154(b) by 1340 days.

(21) Appl. No.: 10/750,390

(22) Filed: Dec. 31, 2003

(65) Prior Publication Data

US 2004/0191305 A1    Sep. 30, 2004

Related U.S. Application Data

(63) Continuation-in-part of application No. 10/448,632, filed on May 30, 2003.

(60) Provisional application No. 60/384,597, filed on May 31, 2002, provisional application No. 60/437,279, filed on Dec. 31, 2002.

(51) Int. Cl.
| | |
|---|---|
| *A61K 47/44* | (2006.01) |
| *A61K 38/28* | (2006.01) |
| *A61K 38/00* | (2006.01) |
| *A61K 38/27* | (2006.01) |
| *A61K 38/23* | (2006.01) |
| *A61K 38/24* | (2006.01) |
| *A61K 38/11* | (2006.01) |
| *A61K 47/00* | (2006.01) |
| *A61K 31/685* | (2006.01) |
| *A61K 38/31* | (2006.01) |
| *A61K 9/127* | (2006.01) |
| *A01N 57/26* | (2006.01) |

(52) U.S. Cl.
USPC ............. 514/5.9; 424/1.21; 424/450; 514/3; 514/78; 514/806; 514/807; 514/808; 514/866; 514/970

(58) Field of Classification Search .................. 424/450; 514/3, 78
See application file for complete search history.

(56) References Cited

U.S. PATENT DOCUMENTS

| | | | | |
|---|---|---|---|---|
| 4,174,296 | A | 11/1979 | Kass | 252/312 |
| 4,614,730 | A * | 9/1986 | Hansen et al. | 514/3 |
| 4,624,665 | A | 11/1986 | Nuwayser | 604/307 |
| 4,687,661 | A * | 8/1987 | Kikuchi et al. | 124/38 |
| 5,120,561 | A | 6/1992 | Silva et al. | 426/531 |
| 5,380,761 | A * | 1/1995 | Szabo et al. | 514/655 |
| 5,391,548 | A * | 2/1995 | Francoeur et al. | 514/212.03 |
| 5,439,967 | A * | 8/1995 | Mathur | 424/450 |
| 5,662,932 | A * | 9/1997 | Amselem et al. | 424/450 |
| 5,674,912 | A | 10/1997 | Martin | 514/724 |
| 5,726,164 | A * | 3/1998 | Weder et al. | 514/80 |
| 5,858,398 | A * | 1/1999 | Cho | 424/450 |
| 5,874,479 | A | 2/1999 | Martin | 514/724 |
| 5,985,298 | A * | 11/1999 | Brieva et al. | 424/401 |
| 6,165,500 | A | 12/2000 | Cevc | 424/450 |
| 6,193,997 | B1 * | 2/2001 | Modi | 424/450 |
| 6,211,250 | B1 | 4/2001 | Tomlinson et al. | 514/772.4 |
| 6,464,987 | B1 * | 10/2002 | Fanara et al. | 424/400 |
| 6,521,250 | B2 | 2/2003 | Meconi et al. | 424/443 |
| 6,538,061 | B2 * | 3/2003 | Chaiyawat et al. | 524/806 |
| 6,555,573 | B2 | 4/2003 | Rosenbloom | 514/456 |
| 2002/0153509 | A1 * | 10/2002 | Lynch et al. | 252/299.01 |

FOREIGN PATENT DOCUMENTS

| | | | |
|---|---|---|---|
| WO | WO 99/56725 | * | 11/1999 |
| WO | WO 01/01963 A1 | | 1/2001 |

OTHER PUBLICATIONS

Cox, Journal of Pesticide Reform 1998, 8(1), p. 30.*
Prescott (Methods in cell Biology 1976, vol. 14 p. 34) 4 pages.*
Phosal 50 PG data sheet Sep. 10, 2007; 1 page.*
Agarwal, R. and Katare, O.P., Preparation and In Vitro Evaluation of Miconazole Nitrate-Loaded Topical Liposomes, *Pharmaceutical Technology*, Nov. 2002, p. 48-60.
Benson, H. and Prankerd, R, "Optimization of Drug Delivery 4. Transdermal Drug Delivery," *Aus J Hosp Pharm*, 27(6): 441-448 (1997).
Bhattacharjee, Y., "More Than the Patch: New Ways to Take Medicine Via Skin," *New York Times*, Jul. 2, 2002, p. F5.
Brannon-Peppas, L., "Polymers in Controlled Drug Delivery," *Medical Plastics and Biomaterials Magazine*, Nov. 1997.
Cevc, G. et al, Transdermal Drug Carriers: Basic Properties, Optimization and Transfer Efficiency in the Case of Epicutaneously Applied Peptides, *Journal of Controlled Release* 36: 3-16 (1995).
Chetty, D. and Chien, Y., Novel Methods of Insulin Delivery: An Update, *Critical Reviews in Therapeutic Drug Carrier Systems*, 15(6): 629-670 (1998).
Christie, W.W., Phosphatidylcholine and Related Lipids, www.lipid.co.uk, May 5, 2003.
Daddona, P., Recent Advances in Peptide, Protein and Macromolecule Drug Delivery, *Current Opinion in Drug Discovery & Development*, 2(2): 168-171 (19999).
Daniels, R., "Galenic Principle's of Modern Skin Care Products," *Skin Care Forum*, Issue 25, Apr. 2001.
Guo et al, "Transdermal Delivery of Insulin in Mice by Using Lecithin Vesicles as a Carrier," *Drug Delivery*, 7:113-116 (2000).
Mitragotri, S., "Synergistic Effect of Enhancers for Transdermal Drug Delivery," *Pharmaceutical Research*, 17(11):1354-1359 (2000).
Patki, V.P. and Jagasia, S.H., "Progress Made in Non-Invasive Insulin Delivery," *Indian Journal of Pharmacology*, 28:143-151 (1996).
Trehan, A. and Ali, A., "Recent Approaches in Insulin Delivery," *Drug Development and Industrial Pharmacy*, 24(7): 589-97 (1998).

* cited by examiner

*Primary Examiner* — Ernst Arnold
(74) *Attorney, Agent, or Firm* — St. Onge Steward Johnston & Reens LLC

(57) ABSTRACT

A method of formulating insulin compositions comprises preparing a carrier having a phosphatidylcholine component which entraps insulin, stabilizing insulin compositions at room temperatures.

8 Claims, No Drawings

METHODS FOR FORMULATING STABILIZED INSULIN COMPOSITIONS

PRIOR APPLICATION

This application is a continuation-in-part of U.S. patent application Ser. No. 10/448,632 filed May 30, 2003, which application is currently pending, and which claims priority to U.S. Provisional Patent Application No. 60/384,597, filed May 31, 2002. Applicant claims priority benefits under 35 U.S.C. §119(e) of U.S. Provisional Patent Application Ser. No. 60/437,279 filed Dec. 31, 2002.

FIELD OF THE INVENTION

The present invention relates to methods of formulating stabilized insulin formulations for topical application.

BACKGROUND OF THE INVENTION

Topical drug delivery systems are known. These systems deliver drugs, therapeutic agents and other desired substances transdermally and may be designed to act locally at the point of application or to act systemically once entering the body's blood circulation. In these systems, delivery may be achieved by means such as direct topical application of a substance or drug in the form of an ointment or the like, or by adhesion of a patch with a reservoir or the like that holds the drug and releases it to the skin in a time-controlled fashion.

Transdermal delivery systems for agents such as drugs, pain relieving compounds, vitamins, and skin improving compounds have been in use for a number of years. These transdermal delivery systems using creams have been developed for use with analgesics and skin refining compounds. Transdermal systems using a patch have been developed for nicotine and estrogen therapies, for instance, estradiol technology described in U.S. Pat. No. 6,521,250 to Meconi, et al.

While effective for their purpose, these systems have typically only been useful for transdermal delivery of relatively small molecules. The skin's porous structure permits such small molecules to pass from the epidermis to the dermis via diffusion. However, large molecules, such as insulin, are not able to diffuse through the skin and cannot be delivered by these known means. One such solution has been provided in U.S. patent application Ser. No. 10/448,632 to Perricone, the disclosure of which is incorporated herein by reference.

While the delivery of large molecules such as insulin have been addressed, such systems do not address the storage and retention of the effectiveness of the drug to be delivered. Many pharmaceuticals and biologically active compounds, such as insulin, must be kept cool and away from heat to remain effective and prevent denaturing at ambient temperatures. Such substances may not be stored or carried (without refrigeration) by the user. Often drugs like insulin must be administered throughout the day and should be in ready-access to or carried by the user, which may expose the compound to high temperatures. As such, there remains a need to stabilize compositions, including insulin, so that they are resistant to warmer temperatures and have a longer life at these temperatures without a need for refrigeration

SUMMARY OF THE INVENTION

A method for formulating stabilized insulin compositions for topical application comprises preparing a carrier having a phosphatidylcholine component and mixing an insulin solution into the carrier to entrap said insulin within said carrier.

DETAILED DESCRIPTION OF THE INVENTION

Phosphatidylcholine is used as a carrier for the formulation of stabilized insulin compositions in the practice of this invention. Phosphatidylcholine is a basic component of cell membrane bilayers and the main phospholipid circulating in the plasma. Phosphatidylcholine is highly absorbable and supplies choline which is needed to facilitate movement of fats and oils across and maintain cell membranes in animals.

Stabilized insulin compositions formulated in accordance with the present invention are non-polar and formulated to contain polypeptides and macromolecules soluble in phosphatidylcholine, which are then applied to skin for transdermal delivery of the macromolecule. Stabilized insulin compositions formulated in accordance with the present invention are efficacious in the delivery of insulin which is conventionally administered intramuscularly or intravenously.

It is an advantage of the invention that topical administration of stabilized insulin compositions formulated according to the present invention and and transdermal delivery of the insulin therein is easier and pleasanter as an administration route than injections, particularly as insulin must be given to patients over a period of time, or for a lifetime. Topical application allows a steady diffusion of the drug to the desired target area without the cyclic dosages typical parenterally administered drugs.

The term "phosphatidylcholine" as used herein means a mixture of stearic, palmitic, and oleic acid diglycerides linked to the choline ester of phosphoric acid, commonly called lecithin. Many commercial lecithin products are available, such as, for example, Lecithol®, Vitellin®, Kelecin®, and Granulestin® because lecithin is widely used in the food industry. Compositions of the invention can contain synthetic or natural lecithin, or mixtures thereof. Natural preparations are preferred because they exhibit desirable physical characteristics and are both economical and nontoxic.

Preferred stable insulin compositions formulated according to the present invention additionally contain polyenylphosphatidylcholine (herein abbreviated "PPC") to enhance epidermal penetration. The term "polyenylphosphatidylcholine" as used herein means any phosphatidylcholine bearing two fatty acid substituents, wherein at least one is an unsaturated fatty acid with at least two double bonds such as linoleic acid. Certain types of soybean lecithin and soybean fractions, for example, contain higher levels of polyenylphosphatidylcholine, with dilinoleoylphosphatidylcholine (18:2-18:2 phosphatidylcholine) as the most abundant phosphatidylcholine species, than conventional food grade lecithin, and are useful in formulating topical drug delivery compositions of the invention. Alternatively, conventional soybean lecithin is enriched with polyenylphosphatidylcholine by adding soybean extracts containing high levels of polyenylphosphatidylcholine. As used herein, this type of phosphatidylcholine is called "polyenylphosphatidylcholine-enriched" phosphatidylcholine (hereinafter referred to as PPC-enriched phosphatidylcholine), even where the term encompasses lecithin obtained from natural sources exhibiting polyenylphosphatidylcholine levels higher than ordinary soybean varieties. These products are commercially available from American Lecithin Company, Rhône-Poulenc and other lecithin vendors. American Lecithin Company markets its products with a "U" designation, indicating high levels of unsaturation; Rhône-Poulenc's product is a soybean extract containing about 42% dilinoleoylphosphatidylcholine and about 24% palmitoyllinoleylphosphatidylcholine (16:0-18:2 PC) as the major phosphatidylcholine components.

While not wishing to be bound to any theory, it is believed that the PPC-enriched phosphatidylcholine forms a bilayer enveloping insulin to create the stabilized insulin compositions, contributing to the stability of the active insulin molecules and enhancing penetration. Further, the stabilized insulin compositions formulated in accordance with the present invention composition may be in liquid crystal phase, with the PPC-enriched phosphatidylcholine loosely arranged in multilamellar fashion, with the polypeptide or macromolecule being bonded and entrapped within the lipid bilayers formed therein. This forms a loosely arranged, yet stable, PPC-enriched phosphatidylcholine-insulin complex that further increases penetration and delivery of the polypeptide or macromolecule to the dermal vasculature.

Stabilized insulin compositions formulated according to the present invention provide an administration route that is a marked improvement over conventional insulin injections, considerably easier and pleasanter. It is a further advantage that insulin compositions formulated according to the present invention are also stable at room temperature, providing considerable convenience for insulin users who, in the past, have had to deal with the refrigerated insulin products commercially available. Also, stabilized insulin compositions formulated according to the present invention have longer shelf lives (whether stored at room temperature or refrigerated) and will not denature at room temperature as would traditional insulin treatments.

Insulin useful in the stabilized insulin compositions formulated according to the present invention is commercially available from a variety of sources, marketed under the tradenames Humulin®, Novolin®, Humalog®, Inutral®, among others. Some of these products contain porcine sequences. Compositions of the invention are preferably formulated with recombinant human polypeptides such as those obtained from Sigma Co., Spectrum Chemicals and Laboratories, and similar vendors and employed in the examples that follow. It is an advantage of the invention that topical drug delivery compositions carrying insulin are formulated with commercially available ingredients.

Stabilized insulin compositions are generally formulated by preparing a carrier having a phosphatidylcholine component, preferable including a PPC-enriched phosphatidylcholine material with the trade name NAT 8729 (commercially available from vendors such as Rhône-Poulenc and American Lecithin Company) and at least one polyglycol (polyhydric alcohol of a monomeric glycol such as Polyethylene glycol (PEG) 200, 300, 400, 600, 1000, 1450, 3350, 4000, 6000, 8000 and 20000), a surfactant such as a siloxylated polyether comprising dimethyl, methyl(propylpolyethylene oxide propylene oxide, acetate) siloxane commercially available from vendors such as Dow Corning (Dow Corning 190 surfactant), silicone fluids such as those containing low viscosity polydimethylsiloxane polymers, methylparaben (p-hydroxy benzoic acid methyl ester) commercially available from vendors such as Down Corning (Dow Corning 200 silicone fluid) and the particular polypeptide(s) or macromolecule(s) in an amount to obtain the desired strength. Additionally, water may be added top the carrier. Insulin from the aforementioned vendors is prepared in N HCl to create an insulin solution. The carrier is then mixed with the insulin solution in an amount to obtain the desired strength of insulin in the final composition. The following examples are presented to further illustrate and explain the present invention and should not be taken as limiting in any regard.

Preparation of Stabilized Insulin Compositions: Example

Stable insulin compositions were formulated by first preparing a base solution. Polyglycol E200 (PEG-200) (50% w/w) was weighed and polyglycol E400 (PEG400) (5% w/w) was added to the same container to obtain the desired weight, (both obtained from Dow Corning). PEG-200 and PEG-400 were lightning mixed at 38-40° C. with IKA model RW20 using a disintegration head impeller slowly at 800 rpm (speed 1), yielding PEG-200/PEG400 solution. A PPC-enriched phosphatidylcholine material denoted NAT 8729 containing 80.6% PPC-enriched phosphatidylcholine and 4.9% lysophosphatidylcholine was obtained from Rhône-Poulenc. NAT 8729 (45% w/w) was shaved and added to PEG-200/PEG-400 solution, covered and mixed, with temperature not exceeding 40° C., until a clear, viscous amber solution with no sediments or separations resulted. The mixing time was approximately five hours. An alternative mixture can be prepared by covering and mixing the solution overnight without heat for a 95-96% yield. The solution was removed from heat and transferred to Ross Homogenizer (Model HSM100LC) using smallest mesh screen.

A Dow Corning Fluid was then prepared. Dow Corning Fluid denominated 190 (1.00% w/w) [a siloxylated polyether comprising dimethyl, methyl(propylpolyethylene oxide propylene oxide, acetate) siloxane] and Dow Corning Fluid denoted 200-5 or 10 cst (1.00% w/w) [silicone fluids containing low viscosity polydimethylsiloxane polymers] were mixed together in a container with a clean spatula.

The solution (53.25% w/w) was warmed to 40° C. and mixed at 800 rpm. Typical mixing times were approximately 5 hours. The solution was then milled at 3800 rpm and the Dow Corning Fluid mixture was added very slowly until the a clear solution resulted. Methyl Paraben (p-hydroxy benzoic acid methyl ester) obtained from Mallinckrodt (0.75% w/w) was added at once and mixed until it dissolved into the solution and a complete solution resulted. Purified water warmed to 40° C. was added very slowly to solution while milling at 7500 rpm for about three minutes. At end of milling, speed was increased to 10,000 rpm for few seconds before stopping. The solution was removed and swept with paddle head using IKA Model RW-20 until cooled to room temperature. This step is very critical and if it is not done properly it will generate a biphasic end product. The general rule is to use a container having a volume twice that of the solution so the homogenizer head is well embedded in the solution. The solution was then cooled to room temperature.

USP human recombinant insulin obtained from Spectrum Chemicals and Laboratories (Product #11247) was prepared in 0.01 N HCl at 50 mg/ml, and gently, yet well mixed. The resulting insulin preparation was added very slowly to the above solution to obtain a final concentration of 500 units/ml or 20 mg/ml. Mixing was continued at room temperature for at least one hour. The final stable insulin composition was stored at 4° C. in amber air-tight container.

RP-HPLC and HPCE analyses of insulin standards (prepared at 5 mg/ml in 0.01 N HCl) and stable insulin compositions of the invention which were stored at different temperatures for different periods of time were performed. The results indicated that standard insulin standards stored at 4° were stable up to 22 weeks and started to denature after 34 weeks, whereas when stored at room temperature started to denature within only 1 week. However, the stable insulin compositions prepared in accordance with the above disclosures that were stored at room temperature were stable up to at least 22 weeks, which is 21 weeks longer than the standard. The results showed no change in shelf-life from the standard for stable insulin compositions stored at 4° C. (no change after 34 weeks).

Stable topical drug delivery compositions of the present invention may be employed to deliver and stabilize polypeptides transdermally, including but not limited to insulin, oxytocin, vasopressin, insulin, somatotropin, calcitonin, chorionic gonadotropin, menotropins, follitropins, somatostatins, progestins, and combinations of any of these. These drugs are readily available from a variety of commercial sources. Somatotropin (pituitary growth hormone) is marketed under the tradenames Gentropin®, Humatrope®, Nutropin®, and Serostim®. A drug delivery composition formulated with somatotropin was formulated in one trial with 85% phosphatidylcholine to which lipoic acid and ascorbyl palmitate were added. Somatotropin readily dispersed in phosphatidylcholine and remained stable in it. Growth hormone appeared to penetrate the skin well when the composition was topically applied.

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention.

What is claimed is:

1. A method of formulating a topical transdermal polypeptide composition comprising:
   providing a polyglycol or a mixture of polyglycols;
   shaving polyenylphosphatidylcholine-enriched phosphatidylcholine into the polyglycol to form a phosphatidylcholine solution; and
   mixing the phosphatidylcholine solution until the phosphatidylcholine solution is clear;
   warming the phosphatidylcholine solution to 40° C. and milling the warmed solution;
   combining siloxylated polyether and polydimethylsiloxane to form a fluid;
   adding the fluid to the warmed solution carrier and milling until the solution is clear;
   adding methyl paraben to the solution and milling until the methyl paraben dis-solves in the solution;
   warming water to 40° C. and adding the warmed water slowly to the solution;
   ceasing milling of the solution and sweeping the solution to cool to room temperature to form a multilamellar liquid crystal carrier;
   mixing a polypeptide solution into the multilamellar liquid crystal carrier to entrap the polypeptide solution within the carrier to form a topical transdermal polypeptide composition in which the polypeptide solution is stabilized at room temperature up to at least 22 weeks.

2. The method of claim 1, wherein the polypeptide solution is a solution of oxytocin, vasopressin, insulin, somatotropin, calcitonin, chorionic gonadotropin, menotropins, follitropins, somatostatins, progestins, and combinations of any of these.

3. The method of claim 2, wherein the polyglycol is a mixture of polyglycols having a molecular weight of 200 and polyglycol having a molecular weight of 400.

4. The method of claim 3, wherein the phosphatidylcholin solution comprises 45% w/w phosphatidylcholine, 50% w/w polyglycol having a molecular weight of 200, and 5% w/w polyglycol having a molecular weight of 400.

5. The method of claim 4, wherein the multilamellar liquid crystal carrier comprises 53.25% w/w phosphatidylcholine solution, 1.00% w/w siloxylated polyether, 1.00% w/w polydimethylsiloxane, 0.75% w/w methyl paraben, and 44.00% w/w water.

6. The method of claim 5, wherein the wherein the siloxylated polyether is dimethyl, methyl(propylpolyethylene oxide propylene oxide, acetate) siloxane.

7. The method of claim 3, wherein the polypeptide solution is a human recombinant insulin solution and the insulin solution is mixed into the multilamellar liquid crystal carrier at room temperature for at least one hour.

8. The method of claim 7, wherein the insulin solution is mixed into the carrier to obtain a topical transdermal insulin composition having a concentration of 20 mg insulin/ml composition.

* * * * *